US006699234B2

(12) United States Patent
Yeh (10) Patent No.: US 6,699,234 B2
(45) Date of Patent: Mar. 2, 2004

(54) LIGHT, THIN, AND FLEXIBLE MEDICATION INFUSION APPARATUSES ATTACHABLE TO USER'S SKIN

(76) Inventor: Show-Way Yeh, 21701 Stevens Creek Blvd., Cupertino, CA (US) 95014

( * ) Notice: Subject to any disclaimer, the term of this patent is extended or adjusted under 35 U.S.C. 154(b) by 167 days.

(21) Appl. No.: 09/810,838

(22) Filed: Mar. 16, 2001

(65) Prior Publication Data

US 2002/0133120 A1 Sep. 19, 2002

(51) Int. Cl.⁷ .................................................. F61K 9/22
(52) U.S. Cl. .................................. 604/890.1; 604/891.1
(58) Field of Search ........................... 604/890.1, 891.1, 604/500, 502, 503, 131, 151, 152, 153, 154, 245, 246, 257, 288.01, 288.02, 288.03

(56) References Cited

U.S. PATENT DOCUMENTS

| | | | | |
|---|---|---|---|---|
| 4,335,835 A | * | 6/1982 | Beigler et al. | 222/95 |
| 4,381,006 A | | 4/1983 | Genese | 604/135 |
| 4,493,704 A | | 1/1985 | Beard | 604/154 |
| 4,585,439 A | | 4/1986 | Michel | 604/155 |
| 4,633,878 A | | 1/1987 | Bombardieri | 600/347 |
| 4,676,122 A | | 6/1987 | Szabo | 74/625 |
| 4,871,351 A | | 10/1989 | Feingold | 604/66 |
| 4,921,487 A | | 5/1990 | Buffet | 604/135 |
| 4,929,234 A | | 5/1990 | Chen | 604/132 |
| 4,931,041 A | | 6/1990 | Faeser | 604/155 |
| 4,997,420 A | | 3/1991 | LeFevre | 604/121 |
| 5,135,500 A | | 8/1992 | Zdeb | 604/143 |
| 5,178,182 A | * | 1/1993 | Kamen | 137/454.2 |
| 5,178,609 A | | 1/1993 | Ishikawa | 604/131 |
| 5,342,313 A | | 8/1994 | Campbell | 604/153 |
| 5,433,704 A | * | 7/1995 | Ross et al. | 604/67 |
| 5,578,005 A | | 11/1996 | Sancoff | 604/82 |
| 5,618,269 A | | 4/1997 | Jacobsen | 604/118 |
| 5,637,095 A | | 6/1997 | Nason et al. | 604/135 |
| 5,643,211 A | | 7/1997 | Sadowski | 604/110 |
| 5,658,252 A | | 8/1997 | Johnson | 604/131 |
| 5,665,065 A | | 9/1997 | Colman | 604/66 |
| 5,785,681 A | | 7/1998 | Indravudh | 604/65 |
| 5,807,337 A | | 9/1998 | Yamada | 604/143 |
| 5,882,343 A | | 3/1999 | Wilson | 604/246 |
| 5,891,096 A | | 4/1999 | Hyun | 604/131 |

(List continued on next page.)

Primary Examiner—Edward K. Look
Assistant Examiner—John K Fristoe, Jr.

(57) ABSTRACT

Four models of apparatuses and their variants are presented. All of them have multiple reservoir cells, a pump, a pump controller, one or more batteries on a flexible pad so that the apparatuses can be adhesive to the user's skin as a big and thick Band-Aid. The user will feel comfortable when he or she bends his to her body. The first model, each reservoir cell contains a medicine bag that contains the medicine. The rest space of the reservoir cells contains the air. Pumping the air into the reservoir cells will press out the medicine from the medicine bags into the user's body. The second model, each reservoir cell contains the medicine and an air bag. Pumping air into the air bags will press out the medicine from the reservoir cells into the user's body. The third model is similar with the second one where the medicine is drawn from the reservoir cells and pressed into the user's body. The forth model is similar with the first one where the medicine is drawn from the medicine bags and pressed into the user'body. The motor and the associated parts is small, simple; and light. The reservoir cells can be small and, hence, the apparatus is thin. Separating the monitor and controller from the apparatus, the apparatus that is attached to the user's skin is even smaller and lighter. Hence, the user will feel much more convenient than using conventional ones.

13 Claims, 4 Drawing Sheets

The cross section view of the conceptual structure where the air is pumped into the reservoir cells to press out the medicine from the medicine bags.

U.S. PATENT DOCUMENTS

| | | | |
|---|---|---|---|
| 5,891,097 A | * 4/1999 | Saito et al. | 604/141 |
| 5,919,167 A | 7/1999 | Mulhanser | 604/131 |
| 5,954,058 A | * 9/1999 | Flaherty | 128/899 |
| 5,957,889 A | 9/1999 | Poulsen | 604/131 |
| 5,957,890 A | 9/1999 | Mann | 604/131 |
| 6,019,747 A | 2/2000 | McPhee | 604/211 |
| 6,045,537 A | 4/2000 | Klitmose | 604/224 |
| 6,088,201 A | 7/2000 | Skinkle | 604/151 |
| 6,099,502 A | 8/2000 | Duchon | 604/131 |
| 6,146,360 A | 11/2000 | Rogers | 604/151 |

* cited by examiner

Fig. 1: The cross section view of the conceptual structure where the air is pumped into the reservoir cells to press out the medicine from the medicine bags.

Fig. 2: The top view of the conceptual structure where the air is pumped into the apparatus to press out the medicine.

Fig. 3: The cross section view of the conceptual structure where the air is pumped into the air bags to press out the medicine from the reservoir cells.

Fig. 4: The cross section view of the conceptual structure where the medicine is drawn from the reservoir cells that also contain the air bags.

Fig. 5: The top view of the conceptual structure where the medicine is drawn from the apparatus.

Fig. 6: The cross section view of the conceptual structure where the medicine is drawn from the medicine bags that are in the reservoir cells.

Fig. 7: The user wearing the medication infusion apparatus adhesive

US 6,699,234 B2

LIGHT, THIN, AND FLEXIBLE MEDICATION INFUSION APPARATUSES ATTACHABLE TO USER'S SKIN

FIELD OF INVENTION

The present invention relates to medication infusion apparatuses carried by the user to continuously deliver medicine into the user's body.

BACKGROUND AND PREVIOUS ARTS

Many of those who need medication constantly and frequently use medication infusion apparatuses. There are two kinds of such apparatuses. The first one, such as disclosed in the U.S. Pat. No. 4,871,351, 4,633,878, 5,785,681, and 5,957,890, the apparatuses are transplanted into the user's bodies. Transplanting artificial devices into a human's body will result in many difficult problems. Hence, these apparatuses are rarely applied to the users.

The apparatuses of the other kind are external to the users and are more practical to most users. Examples include the MiniMed 508 insulin pump produced by MiniMed and those disclosed in the U.S. Pat. Nos. 6,146,360, 6,099,502, 6,083,201, 6,045,537, 6,019,747, 5,957,889, 5,919,167, 5,891,096, 5,882,343, 5,807,337, 5,665,065, 5,658,252, 5,643,211, 5,637,095, 5,618,269, 5,578,005, 5,342,313, 5,178,609, 5,135,500, 4,997,420, 4,931,041, 4,929,234, 4,921,487, 4,676,122, 4,585,439, 4,493,704, 4,381,006. All these apparatuses have a main apparatus that is linked to a needle or cannula directly or via a pipe. The main apparatus includes a reservoir, a syringe, or the similar to hold the medication to be delivered to the user. It also includes all the mechanics to force and to administrate the medication to be delivered. It is large, heavy, thick, and hard that the user feels very inconvenient because he or she feels to be connected to a heavy object via a pipe. It is inconvenient to carry such a device. My previous invention "Medicine Delivery Apparatus with Flat Reservoir" with application Ser. No. 09/654239 filed on Sep. 2 2000 is the only means that presents a conceptual apparatus that the users can tape the apparatus to their skin. However, it is hard. Bending the body, the user will feel uncomfortable.

The U.S. Pat. No. 5,954,058 proposed an implantable apparatus where the medicine is refilled and the medicine container is not replaced. The apparatus is a whole hard piece. It is not to be carried under the user's clothes or attached to the user's skin.

The U.S. Pat. No. 5,891,097 proposed an apparatus where the medicine is pressed out of the apparatus by the gas generated by an electrochemical device. The voltage of the current applied to the electrochemical device is much higher than the flat battery. Hence, the apparatus is uncomfortable to be carried under the user's clothes or attached to the user's skin.

The U.S. Pat. No. 5,433,704 proposed an apparatus where the medicine is in a flexible bag and is pressed out of the bag by the fluid pumped in the bladder inside of the medicine bag. Since the medicine bag is flexible, the medicine pressed out when the medicine bag reaches the housing box and before that may be different. This will make the design more complicated. Furthermore, this invention is designed to be a whole hard piece. It is very uncomfortable for the user to carry it under the clothes or to attach it to the skin.

The U.S. Pat. No. 5,178,182 proposed a valve device using a membrane to seal the fluid inlet. The membrane is controlled by another pump-type device that needs another valves. The valve of this invention can be small but the overall apparatus is not if this invention is used for medicine infusion system. The medicine infusion system may not use this kind of valves. My present invention does not use it.

The U.S. Pat. No. 4,335,835 proposed an infusion apparatus for constant rate. The apparatus is large and is not used under the user's clothes or attached to the user's skin. It is very uncomfortable for the user to carry it under the clothes or to attach it to the skin.

My present invention is different from all of the above in that the apparatus of my present invention is thin, flat, and flexible. The user will be comfortable to carry it under the clothes or to attach it to the skin. Other people will not notice that the user uses it unless the user shows it to others.

The users will feel much more convenient if the apparatuses are light, thin, flexible, and bendable to be comfortably taped to their skin. Then, they just feel like to use a large and thick Band-Aid. My present invention is to solve all the problems above.

The monitor and controller of the medication infusion apparatus can be separated from the main device to give the user more convenience.

OBJECTS AND ADVANTAGES

My present invention presents conceptual medication infusion apparatuses that are light, thin, and flexible enough to be attached to the user' skin. FIG. 9 shows a user wearing the apparatus. The medication infusion apparatus 10 is adhesive to the user's skin 355. The medication is delivered to the user via the converging pipe 31 and the needle or cannula 335. The converging pipe 31 is taped to the user's skin 355 by a tape 25. The users will feel like to use a big and thick Band-Aid. Or, use a band to tie the apparatus to the body. Or, the user just carries the apparatus under the clothes. Since everything is attached to the skin, they no longer feel to be connected to an external extra object via a pipe and feel much more convenient.

REFERENCE NUMERALS IN DRAWINGS

10: The medication infusion apparatus.
25: The tape to tape the medicine pipe to the user's skin.

30: The medicine pipes.
31: The converging pipe where the medicine in all medicine pipes converges to this pipe.
40: The air pipes.
50: The air pump.
51: The medicine pump.
52: The air pump controller.
53: The medicine pump controller.
55: The monitor and controller of the medication infusion apparatus.
58: The flexible cable to connect the batteries and either the air pump controller or the medicine pump controller.
59: The flexible cable to connect the air pump controller and the air pump or the medicine pump controller and the medicine pump.
60: The flexible adhesive pad.
62: The batteries.
110: The reservoir cell or cells.
120: The air bag or bags.
121: The medicine bag or bags.
335: The needle or the cannula that inserts into the user's body to deliver medicine.
355: The user's skin.

SUMMARY

My present invention presents four models of apparatuses and their variants that are light, thin, flexible, and bendable to be adhesive to the user's skin. All of them have a number of reservoir cells on a flexible pad. The first model, each reservoir cell contains a medicine bag that contains the medicine. The rest space of the reservoir cells contains the air. Pumping the air into the reservoir cells will press out the medicine from the medicine bags into the user's body. The second model, each reservoir cell contains the medicine and an air bag. Pumping air into the air bags will press out the medicine from the reservoir cells into the user's body. The third model is similar with the second one where the medicine is drawn from the reservoir cells. The forth model is similar with the first one where the medicine is drawn from the medicine bags. The motor and the associated parts of these apparatuses is small, simple, and light. The reservoir cells can be small and, hence, the apparatuses are thin. The pad that the reservoir cells are built on is flexible and there is gap between adjacent reservoir cells. The pump, the pump controller, and the batteries are separated and linked by flexible cables so that the overall apparatus is thin and bendable. Hence, the apparatuses can be adhesive to the user' skin and the users will feel comfortable while they bend their bodies. Furthermore, separating the monitor and controllers from the apparatuses, the apparatuses that are attached to the user's skin are even smaller and lighter. The users will feel like using a large and thick Band-Aid. Hence, the users will feel much more convenient than using the conventional ones.

DESCRIPTION

Figure 1:
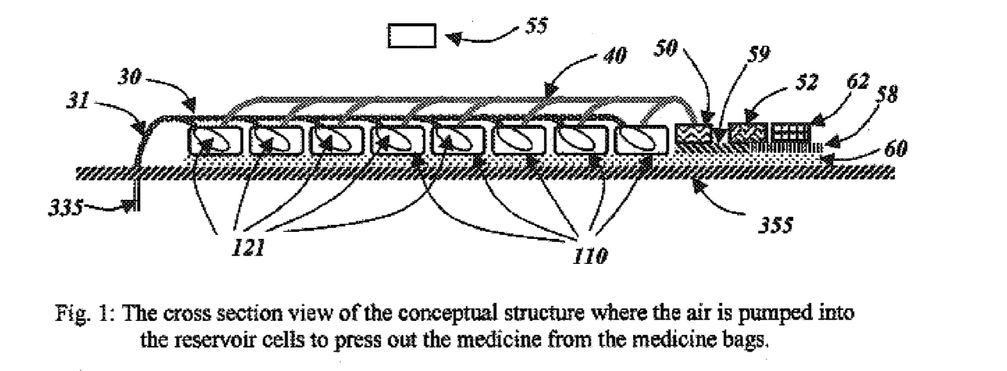
FIG. 1: The cross section view of the conceptual structure of the apparatus where the air is pumped into the reservoir cells to press out the medicine from the medicine bags.
Figure 2:
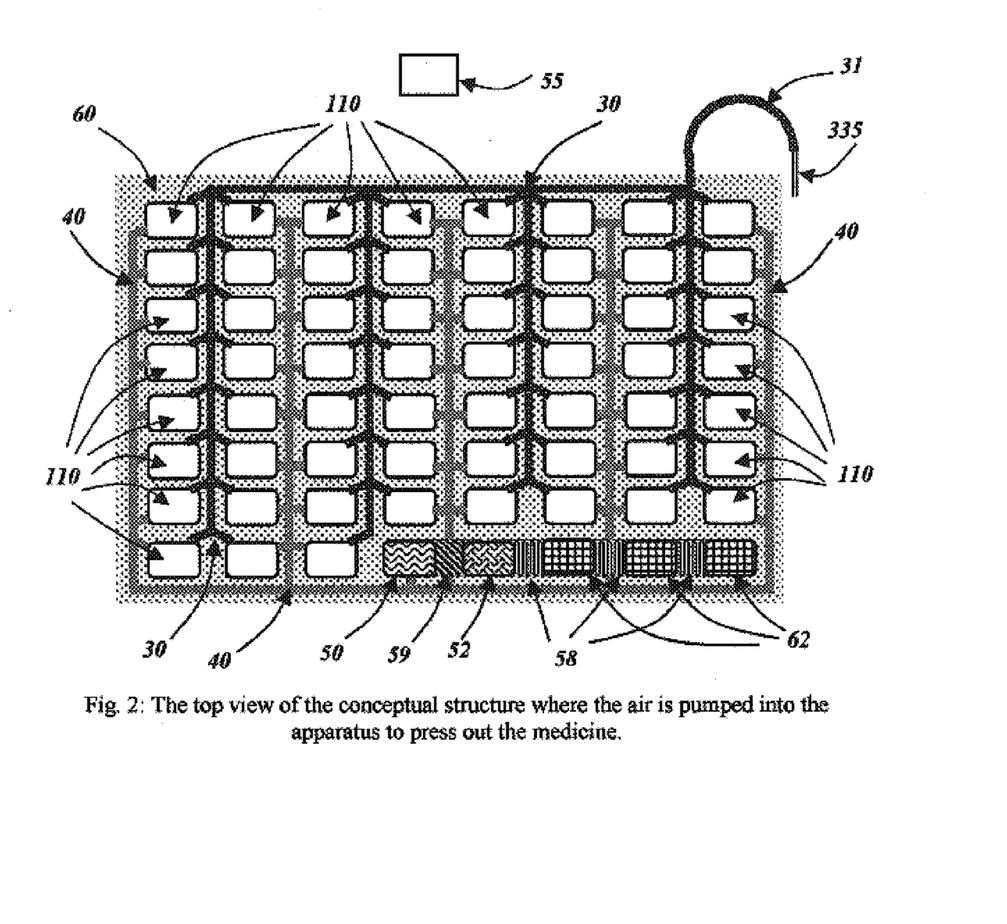
FIG. 2: The top view of the conceptual structure of the apparatus where the air is pumped into the reservoir cells to press out the medicine.

The present invention discloses conceptual structures of the apparatuses that are light, thin, and flexible enough to be attached to the user's bodies. The basic idea is as follows: Install multiple small and hard reservoir cells on a flexible adhesive pad so that the pad is attached to the user's skin and the user feels comfortable when he or she bends his or her body. Install a bag in each reservoir cell. The bags may contain the medicine and the rest space of the reservoir cells contains the air. Or, the bags contain the air and the rest space of the reservoir cells contains the medicine. The medicine may be drawn out directly. Or, the air may be pumped in to press out the medicine. Therefore, there are four models. The details are as follows:

FIG. 1 shows the vertical cross section view of the conceptual structure of the first model. FIG. 2 shows the top view of the same model. There are a number of small, hard, and sealed reservoir cells 110 that are installed on a flexible adhesive pad 60. They can be arranged to be a two-dimensional array as FIG. 2 shows. The flexible adhesive pad 60 is adhesive to the user's skin 355 as FIG. 9 shows. The dimension of each reservoir cell 110 is small so that the apparatus is thin. Each reservoir cell 110 is hard enough so that the inside pressure will not change when it is pressed. The gap between adjacent reservoir cells 110 is to let the overall apparatus be bendable.

There is a medicine bag 121 in each reservoir cell 110. The medicine bags 121 contain the medicine to be delivered into the user's body and are so soft and flexible that they require negligible force to transfer the force from one side to the other. The rest space in all reservoir cells 110 is mainly air.

All reservoir cells 110 are linked to the air pump 50 via the air pipes 40. So that the pressure in all reservoir cells 110 is the same. All medicine bags 121 are linked to the needle or cannula 335 via the medicine pipes 30 and the converging pipe 31. The needle or cannula 335 inserts into the users body to deliver the medicine. The air pump controller 52 controls the air pump 50 to pump finite amount of air to spread to all reservoir cells 110 through the air pipes 40. This will increase the pressure in all reservoir cells 110. Hence the medicine is pressed out from all medicine bags 121 into the users body through the medicine pipes 30, the converging pipe 31, and the needle or cannula 335. There is a valve in the air pump 50 or in the air pipes 40 to prevent from that the air flows backward. The valve is not shown in the figure. The air pipes 40 and the medicine pipes 30 are drawn to be above the reservoir cells 110 in FIG. 1 for clearness. They can be installed in the flexible pad 60 or between the reservoir cells 110 as FIG. 2 shows as long as the pressure in these pipes will not change when the users bend their bodies.

Water may be pumped into the reservoir cells 110 when the apparatus is wet. It is all right as long as the volume of the water is the same as the volume of the air to be pumped in. So, in general, all kinds of fluid can be pumped into the reservoir cells 110 as long as the volume is finite and controllable. However, mainly, the air is used.

The monitor and controller 55 accepts commands from the user about when and how much the user wants the medicine to be delivered. It sends instructions at appropriate moment to the air pump controller 52 to pump the right amount of air into the reservoir cells 110 according to the user's desire. So that the air pump controller 52 controls the air pump 50 to do it. Hence, the right amount of medicine is delivered into the user's body at the right moment. The functions of the monitor and controller 55 and the air pump controller 52 depend on design. The monitor and controller 55 also collects information reported from the air pump controller 52 and shows the information of the whole apparatus to the user. The communication channel between the monitor and controller 55 and the air pump controller 52 can be wireless as FIGS. 1 and 2 show, or wired, or both where it is wired when a cable connects them and is wireless when the cable is disconnected.

The sizes of the air pump 50, the air pump controller 52, and the batteries 62 depend on the design. Each of them is installed in a hard case on the flexible pad 60. The air pump controller 52 and the batteries 62 are linked by a flexible cable 58 as shown in FIGS. 1 and 2. The batteries 62 provide electricity to the air pump controller 52 via the flexible cable 58. The number of batteries 62 depends on design. There are three in FIG. 2 and only one in FIG. 1 just to illustrate the concept. Any number of batteries 62 is all right. The air pump 50 and the air pump controller 52 are linked by a flexible cable 59 as shown in FIGS. 1 and 2. The air pump controller 52 determines when the current is forwarded to air pump 50 via the flexible cable 59 and when the current is stopped. The air pump controller 52 also collects information from the air pump 50 via the flexible cable 59. Since the cables 58 and 59 are flexible, the whole apparatus is flexible. How to separate the air pump 50 and the air pump controller 52 depends on design. If the air pump controller 52 is too big, it can be divided into two or more parts linked by flexible cable. The geometry arrangement of the reservoir cells 110, the air pump 50, the air pump controller 52, and the batteries 62 is arbitrary.

The medicine bags 121, the medicine pipes 30, and the converging pipe 31 can be filled in the medicine as a cartridge when the apparatus is manufactured. It is easy to replace cartridges. The medicine can also be filled when the apparatus is to be used. The medicine can be drawn from the medicine bottle by a syringe and then be injected into the medicine bags 121 via the converging pipe 31 and the medicine pipes 30. The needle or cannula 335 and the converging pipe 31 may be disconnected and the air valve is open originally. The syringe having the medicine may be connected to the converging pipe 31 to inject the medicine into the medicine bags 121. The reservoir cells 110, the medicine bags 121, the medicine pipes 30, and the converging pipe 31 are preferably made of transparent material so that the air in these parts is visible. Holding the apparatus up and turning it so that the converging pipe 31 is at the top position will let the air flow up. The air can be drawn by the syringe or be primed out by using the air pump 50. The filling and the drawing or priming procedures may repeat few time to get rid of the air. Then, connect the converging pipe 31 and the needle or cannula 335 and prime out the air in the needle or cannula 335. Finally, turn the air valve to the normal position. Another way to fill in the medicine is as follows. The converging pipe 31 is connected to a needle that is inserted into the medicine bottle. Using another air pipe to connect the inlet of the air pump 50 and a needle that is also inserted into the medicine bottle. Let the air pump 50 work reverse so that it draws out the air from the reservoir cells 110 and pumps the air into the medicine bottle. Hence, the medicine is pressed out from the medicine bottle into the medicine bags 121. The method to get rid of the air from the medicine bags 121, the medicine pipes 30, and the converging pipe 31 is the same as above.

Figure 3:
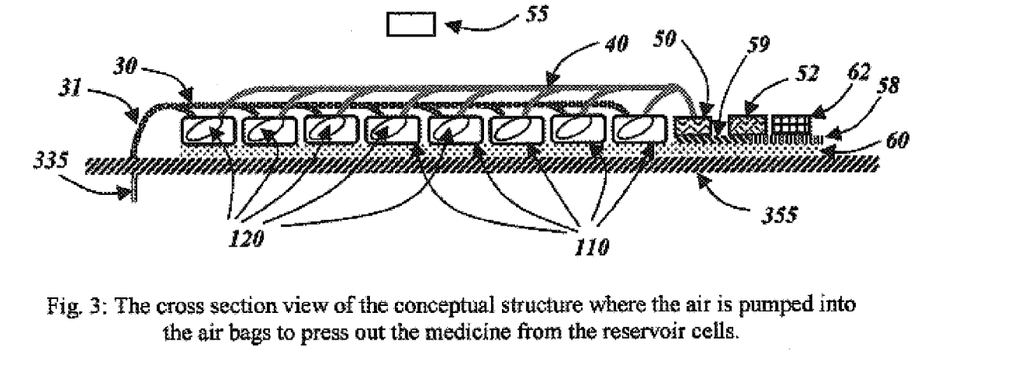
FIG. 3: The cross section view of the conceptual structure of the apparatus where the air is pumped into the air bags to press out the medicine from the reservoir cells.

FIG. 3 shows the vertical cross section view of the conceptual structure of the second model. The top view is the same as FIG. 2 because the difference of these two models is only in the reservoir cells 110. There is an air bag 120 in each reservoir cell 110. The air bags 120 contain the air. The rest space in all reservoir cells 110 is filled with the medicine to be delivered into the user's body. The air bags 120 are so soft and flexible that they require negligible force to transfer force from one side to the other. All reservoir cells 110 are linked to the needle or cannula 335 via the medicine pipes 30 and the converging pipe 31. All air bags 120 are linked to the air pump 50 via the air pipes 40. The air pump controller 52 controls the air pump 50 to pump the air to spread to all air bags 120 through the air pipes 40. Hence the medicine is pressed out from all reservoir cells 110 into the user's body through the medicine pipes 30, the converging pipe 31, and the needle or cannula 335.

The flexible adhesive pad 60, the air pump controller 52, the monitor and controller 55, the batteries 62, and the cables 58 and 59 work the same as in the first model.

Note that the difference between this model and the apparatus presented in my invention "Medicine Delivery Apparatus with Flat Reservoir" with application Ser. No. 09/654239 is the following. Each of the reservoir cells 110, the air pump 50, the air pump controller 52, and the batteries 62 of the former is individually installed on a flexible pad. Hence, the overall apparatus is bendable. For the later, all of them are installed in a hard case. Hence, the apparatus is not bendable.

The reservoir cells 110, the medicine pipes 30, and the converging pipe 31 can be filled in the medicine as a cartridge when the apparatus is manufactured. The medicine can also be filled when the apparatus is to be used. The methods to do so and to get rid of the air are the same as the first model except that the medicine is filled in the reservoir cells 110.

Figure 4:
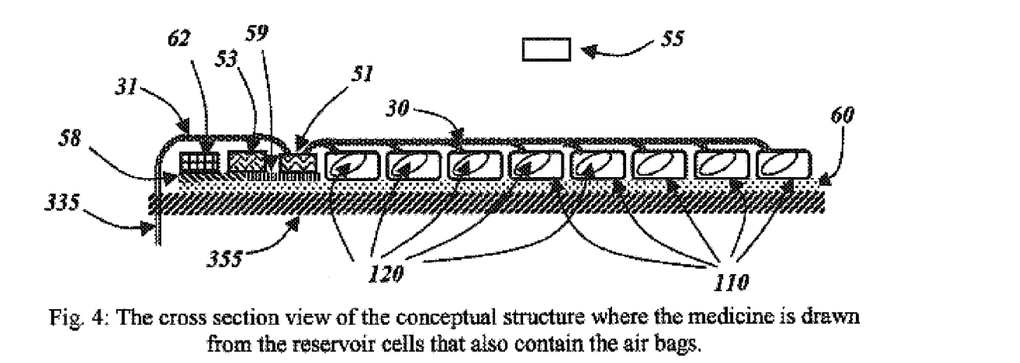
FIG. 4: The cross section view of the conceptual structure of the apparatus where the medicine is drawn from the reservoir cells that also contain the air bags.
Figure 5:
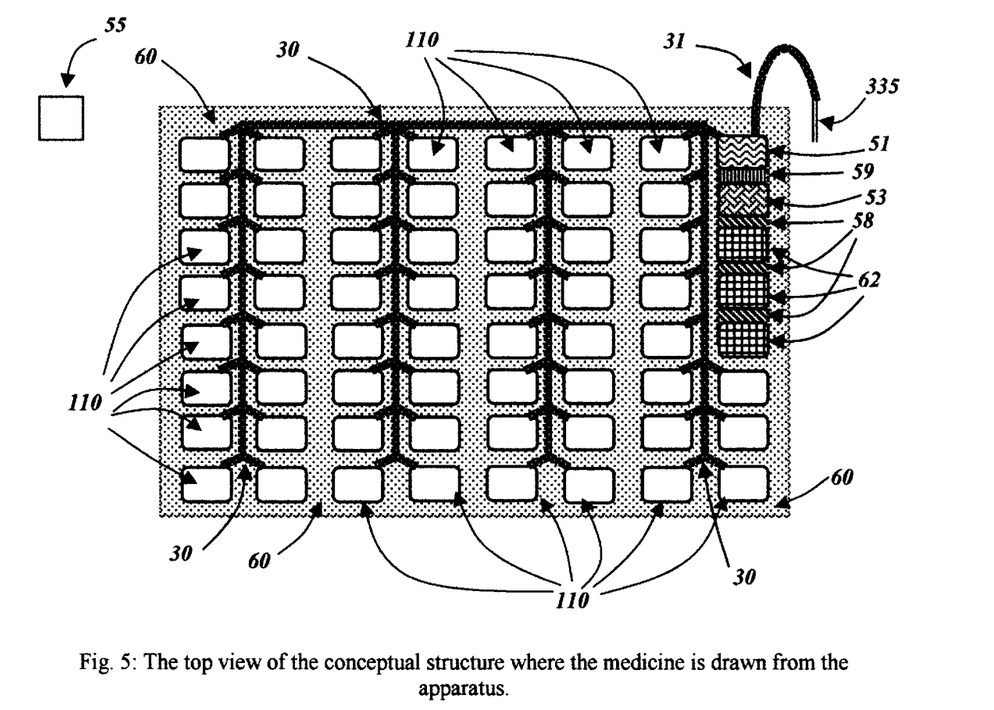
FIG. 5: The top view of the conceptual structure of the apparatus where the medicine is drawn from the reservoir cells.

FIG. 4 shows the vertical cross section view of the conceptual structure of the third model. FIG. 5 shows the top view of the same model. There are a number of small and hard reservoir cells 110 that are installed on a flexible adhesive pad 60. They can be arranged to be a two-dimensional array as FIG. 5 shows. The flexible adhesive pad 60 is adhesive to the user's skin 355. The dimension of each reservoir cell 110 is small so that the apparatus is thin. The gap between adjacent reservoir cells 110 is long enough so that the overall apparatus is bendable.

There is an air bag 120 in each reservoir cell 110. The air bags 120 contain the air. The rest space in all reservoir cells 110 is filled with the medicine. Each air bag 120 has a small hole open to the outside of the reservoir cell 110 to let the air flow in. Each reservoir cell 110 is hard enough so that, when it is pressed, the pressure of the medicine will not change. All reservoir cells 110 are linked to the medicine pump 51 via the medicine pipes 30. The medicine pump controller 53 controls the medicine pump 51 to draw the medicine from all reservoir cells 110 through the medicine pipes 30 and to press the medicine into the user's body through the converging pipe 31 and the needle or cannula 335. The air will flow into the air bags 120 through the holes to balance the pressure in the reservoir cells 110. The air bags 120 may be linked by the air pipes as the second model.

The monitor and controller 55 works the same as in the first model except that it communicates with the medicine pump controller 53 instead of the air pump controller. The flexible adhesive pad 60, the flexible cables 58 and 59, and the batteries 62 are the same as in the first model.

The reservoir cells 110 and the medicine pipes 30 can be filled in the medicine as a cartridge when the apparatus is manufactured. When it is to be used, connect the cartridge to the medicine pump 51 and prime out the air in the converging pipe 31 and the needle or cannula 335. The medicine can also be filled in when the apparatus is to be used. The needle or cannula 335 and the converging pipe 31 may be disconnected originally. The converging pipe 31 connects to a needle that inserts into the medicine bottle. The medicine pump 51 works reverse to draw the medicine from the medicine bottle and to press the medicine into the reservoir cells 110. While the air in the reservoir cells 110 and in the medicine pipes 30 flows up, the medicine pump 51 works forward to get rid of the air in these parts. Another way to fill up the medicine is to disconnect the medicine pipes 30 from the medicine pump 51 or to connect another medicine pipe to the medicine pipes 30 and then to use a syringe to do it as described above. After the medicine is filled up, the additional medicine pipe is shut off. For all methods, connecting the needle or cannula 335 and the converging pipe 31 and priming out the air in the converging pipe 31 is the last step.

Figure 6:
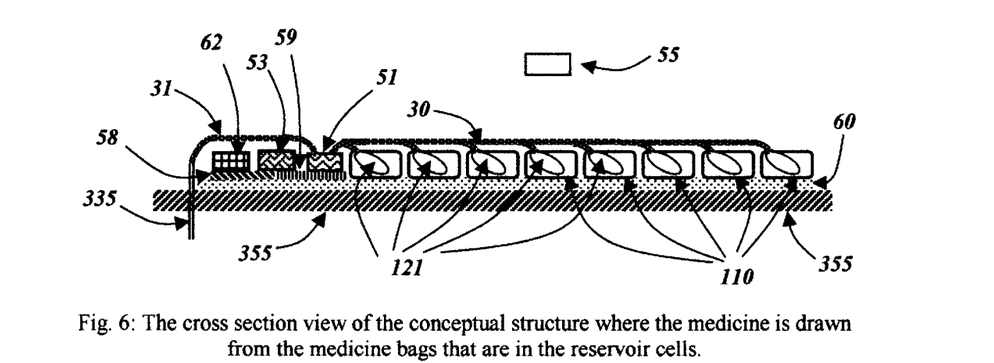
FIG. 6: The cross section view of the conceptual structure of the apparatus where the medicine is drawn from the medicine bags that are in the reservoir cells.
Figure 7:
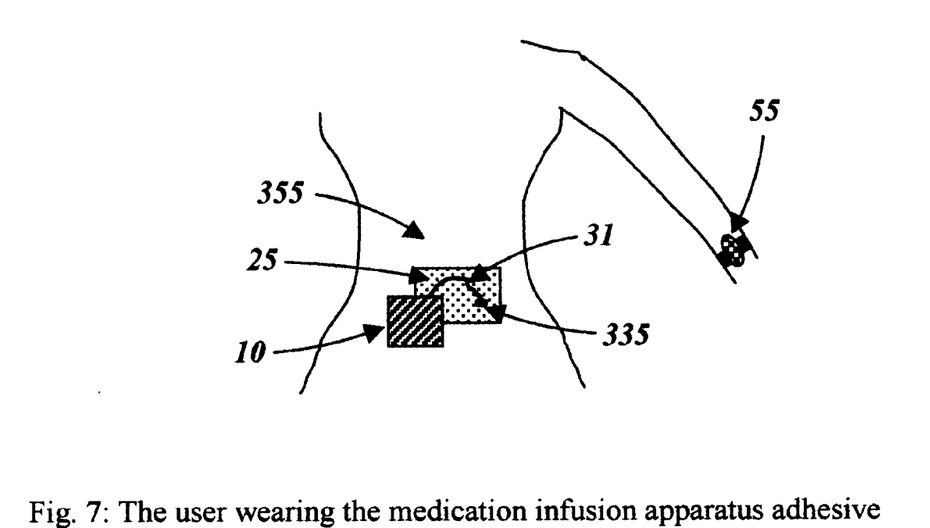
FIG. 7: The user wearing the medication infusion apparatus adhesive.

FIG. 6 shows the vertical cross section view of the conceptual structure of the forth model. The top view is the same as FIG. 5 because the difference of the third and the forth models is in the reservoir cells 110. There are a number of small and hard reservoir cells 110 that are installed on a flexible adhesive pad 60. There is a medicine bag 121 in each reservoir cell 110. The medicine bags 121 contain the medicine. The rest space in each reservoir cell 110 is filled with the air. All reservoir cells 110 have small holes to let the air flow in. All medicine bags 121 are linked to a medicine pump 51 via the medicine pipes 30. The medicine pump controller 53 controls the medicine pump 51 to draw the medicine from all medicine bags 121 through the medicine pipes 30 and to press the medicine into the user's body through the converging pipe 31 and the needle or cannula 335. The air will flow into the reservoir cells 110 through the holes to balance the pressure in the reservoir cells 110.

The monitor and controller 55, the medicine pump controller 53, the flexible adhesive pad 60, the flexible cables 58 and 59, and the batteries 62 are the same as in the third model.

The medicine bags 121 and the medicine pipes 30 can be filled in the medicine as a cartridge when the apparatus is manufactured. The medicine can also be filled when the apparatus is to be used. The methods to do so and to get rid of the air are the same as the third model except that the medicine is filled in the medicine bags 121.

In all four models above, the motor with its associated parts to pump the air or to draw the medicine is small and simple and, hence, is light. It is much lighter than that of the conventional ones that have pistons and plungers in the reservoirs. Separating the monitor and controller 55 from the reservoir cells 110, the pump 50 or 52, the pump controller 51 or 53, and the batteries 62, the apparatus that attaches to the user's skin is even lighter. The gap between adjacent embodiments of the reservoir cells 110, the pump 50 or 52, the pump controller 51 or 53, and the batteries 62 is to let the apparatus that attaches to the user's skin be bendable. Hence, the user will not feel uncomfortable when he or she bends his or her body.

When the user jumps or exercises, the medicine in the reservoir cells 110 or in the medicine bags 121 is shacked. That may cause bubbles in the medicine. There are few ways to reduce this effect. The reservoir cells 110 can be made small enough to do it. Each reservoir cell 110 may further be divided into smaller cells that contain smaller air or medicine bags, small enough to do it. Each reservoir cell 110 may be made to be a narrow tunnel that contains a narrow air or medicine bag, narrow enough to do it. Or, combine these methods.

If the medication dosage is small, one reservoir cell 110 may be all right. If the sizes of any of the pump 50 or 52, the pump controller 51 or 53, and the batteries 62, are small, they may be installed as one embodiment.

CONCLUSION

Accordingly, the readers will see that the closure of this invention can be used to continually deliver medicine for the users. Comparing to the conventional medicine pumps and the prior disclosed apparatuses; the apparatus using my invention has the following advantages:

it is flexible;
it is lighter; and
it is thinner.

Separating the monitor and controller from the apparatus, it is even smaller, lighter, and thinner. The apparatus can be adhesive to the user's skin, just like using a big and thick Band-Aid, tied to the user's body, or carried under the user's clothes. This will give the users much more convenience than the conventional ones.

Although the description above contains many specifications, these should not be constructed as limiting the scope of the invention but as merely providing illustrations of some of the presently preferred embodiments of this invention. Thus the scope of the invention should be determined by the appended claims and their legal equivalents, rather than by the examples given.

I claim:

1. A thin and bendable medicine infusion apparatus attachable to the user's skin or carried under the user's clothes comprising:

a monitor and controller composed of separated compartments linked with soft cables;

an air pump for pumping the air when supplied with commands; any number of thin and small reservoir cells each including:
  a flexible membrane which is transformable by a pressure of the air;
  a medicine compartment and an air compartment which are formed in said reservoir cell by said membrane;
  a medicine delivery portion in said reservoir cell for delivering the medicine into or out of said medicine compartment; and
  an air introduction portion in said reservoir cell for delivering the air pumped by said air pump into said air compartment;

soft cables linking said monitor and controller and said air pump;

soft air pipes linking all said air introduction portion and said air pump; and soft medicine pipes linking all said medicine delivery portion and the insertion device;

wherein the air pumped by said air pump is introduced into said air compartments through said air introduction portions to increase the inner pressure of said air compartments to press said membranes, the medicine in said medicine compartments is delivered through said medicine delivery portions by the pressure of said membranes, and said medicine infusion apparatus is bendable.

2. The thin and flexible medication infusion apparatus of claim 1 wherein:

said membrane is a medicine bag containing the medicine;

said medicine compartment is in said medicine bag; and said air compartment is in said reservoir cell and out of said medicine bag wherein the air pumped by said air pump is introduced into said reservoir cells through said air introduction portions to increase the inner pressure of said reservoir cells to press said medicine bags, the medicine in said medicine bags is delivered through said medicine delivery portions by the pressure of said medicine bags, and said medicine infusion apparatus is bendable.

3. The thin and flexible medication infusion apparatus of claim 1 wherein:

said membrane is an air bag containing the air;

said air compartment is in said air bag; and said medicine compartment is in said reservoir cell and out of said air bag;

wherein the air pumped by said air pump is introduced into said air bags to increase the inner pressure of said air bags to press said air bags, the medicine in said reservoir cells is delivered through said medicine delivery portion by the pressure of said air bags, and said medicine infusion apparatus is bendable.

4. A thin and bendable medicine infusion apparatus attachable to the user's skin or carried under the user's clothes comprising:

a monitor and controller composed of separated compartments linked with soft cables;

an medicine pump for drawing the medicine when supplied with commands;

any number of thin and small reservoir cells each including:

a flexible membrane which is transformable by a pressure of the air;

a medicine compartment and an air compartment which are formed in said reservoir cell by said membrane;

a medicine delivery portion in said reservoir cell for delivering the medicine into or out of said medicine compartment; and an air introduction portion in said reservoir cell for delivering the air pumped by said air pump into said air compartment;

soft cables linking said monitor and controller and said medicine pump; and soft medicine pipes linking all said medicine delivery portion and said medicine pump;

wherein the medicine in said medicine compartments is drawn out of said medicine compartments through said medicine delivery portions by said medicine pump to decrease the inner pressure of said medicine compartments to extract said membranes, the inner pressure of said air compartments is decreased, the air is sucked into said air compartments through said air introduction portions, and said medicine infusion apparatus is bendable.

5. The thin and flexible medication infusion apparatus of claim 4 wherein:

said membrane is a medicine bag containing the medicine;

said medicine compartment is in said medicine bag; and said air compartment is in said reservoir cell and out of said medicine bags wherein the medicine in said medicine bags is drawn out of said medicine bags through said medicine delivery portions by said medicine pump to decrease the inner pressure of said medicine bags to extract said membranes, the inner pressure of said reservoir cells is decreased, the air is sucked into said reservoir cells through said air introduction portions, and said medicine infusion apparatus is bendable.

6. The thin and flexible medication infusion apparatus of claim 4 wherein:

said membrane is an air bag containing the air;

said air compartment is in said air bag; and said medicine compartment is in said reservoir cell and out of said air bag;

wherein the medicine in said reservoir cells is drawn out of said reservoir cells through said medicine delivery portions by said medicine pump to decrease the inner pressure of said air bags to extract said air bags, the inner pressure of said air bags is decreased, the air is sucked into said air bags through said air introduction portions, and said medicine infusion apparatus is bendable.

7. The thin and flexible medication infusion apparatus as in any one of claims 2 and 5 wherein:

each said reservoir cell is further divided into cellular air cells; and each said cellular air cell contains a cellular medicine bag.

8. The thin and flexible medication infusion apparatus as in any one of claims 2 and 5 wherein:

each said medicine bag is a narrow medicine bag; and each said reservoir cell is a narrow tunnel containing said narrow medicine bag.

9. The thin and flexible medication infusion apparatus of claim 7 wherein each said cellular air cell is a narrow tunnel containing said cellular medicine bag.

10. The thin and flexible medication infusion apparatus as in any one of claims 3 and 6 wherein:

each said reservoir cell is further divided into cellular medicine cells; and each said cellular medicine cell contains a cellular air bag.

11. The thin and flexible medication infusion apparatus as in any one of claims 3 and 6 wherein:

each said air bag is a narrow air bag; and each said reservoir cell is a narrow medicine tunnel containing one said narrow air bag.

12. The thin and flexible medication infusion apparatus of claim 10 wherein each said cellular medicine cell is a narrow medicine tunnel containing said cellular air bag.

13. The thin and flexible medication infusion apparatus as in any one of claims 1, and 4, wherein said reservoir cells are install on a flexible pad.

* * * * *